US012697249B2

(12) United States Patent　　　　(10) Patent No.:　US 12,697,249 B2
Govari et al.　　　　　　　　　　　　(45) Date of Patent:　　　Aug. 4, 2026

(54) IRRIGATION IN A PHACOEMULSIFICATION SYSTEM

(71) Applicant: JOHNSON & JOHNSON SURGICAL VISION, INC., Irvine, CA (US)

(72) Inventors: Assaf Govari, Haifa (IL); Eran Aharon, Haifa (IL); Yehuda Algawi, Binyamina (IL); Ilya Sitnitsky, Nahariya (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 1001 days.

(21) Appl. No.: 17/715,091

(22) Filed: Apr. 7, 2022

(65) Prior Publication Data

US 2022/0395395 A1　　Dec. 15, 2022

Related U.S. Application Data

(60) Provisional application No. 63/210,585, filed on Jun. 15, 2021.

(51) Int. Cl.
　　*A61F 9/007*　　　　(2006.01)
　　*A61M 1/00*　　　　(2006.01)
(52) U.S. Cl.
　　CPC ........... *A61F 9/00745* (2013.01); *A61M 1/74* (2021.05); *A61M 1/77* (2021.05); *A61M 2210/0612* (2013.01)
(58) Field of Classification Search
　　CPC ....... A61F 9/00745; A61M 1/77; A61M 1/74; A61M 2210/0612; A61M 2206/22; A61B 17/320068; A61B 2017/320084
(Continued)

(56) References Cited

U.S. PATENT DOCUMENTS 2,140,737 A　　12/1938　Griffith
2,815,838 A　　12/1957　Dodge
(Continued)

FOREIGN PATENT DOCUMENTS

CN　　　209370050 U　　9/2019
CN　　　111609054 A　　9/2020
(Continued)

OTHER PUBLICATIONS

Co-pending U.S. Appl. No. 17/318,665, filed May 12, 2021.

*Primary Examiner* — Devon C Kramer
*Assistant Examiner* — Kelsey L Stanek

(57)　　　　　ABSTRACT

In one example, a phacoemulsification system includes a phacoemulsification probe including a distal end comprising a needle, and a piezoelectric crystal configured to vibrate the needle so as to emulsify a lens of an eye, an irrigation reservoir configured to store irrigation fluid, an irrigation line extending from the irrigation reservoir to the distal end of phacoemulsification probe, a pumping sub-system configured to pump the irrigation fluid from the irrigation reservoir to the distal end of the phacoemulsification probe via the irrigation line, and a pressure damping insert disposed in the irrigation line between the pumping sub-system and the distal end, and comprising multiple paths therethrough configured to divide a flow of the irrigation fluid entering the pressure damping insert in order to dampen pressure elevations in the irrigation fluid exiting the pumping sub-system.

11 Claims, 2 Drawing Sheets

(58) Field of Classification Search
USPC ........................................................ 604/22
See application file for complete search history.

(56) References Cited

U.S. PATENT DOCUMENTS

| | | | |
|---|---|---|---|
| 2,872,225 | A | 2/1959 | Walker, Jr. |
| 3,174,598 | A | 3/1965 | Mattson |
| 4,204,411 | A | 5/1980 | Jeanson |
| 4,256,442 | A | 3/1981 | Lamadrid et al. |
| 4,386,654 | A | 6/1983 | Becker |
| 4,591,322 | A | 5/1986 | Ono et al. |
| 4,714,803 | A | 12/1987 | Lederman |
| 4,990,070 | A | 2/1991 | Maruyama |
| 5,085,564 | A | 2/1992 | Naylor et al. |
| 5,246,414 | A | 9/1993 | Hallbach |
| 5,288,271 | A | 2/1994 | Nelson et al. |
| 5,295,788 | A | 3/1994 | Tajima et al. |
| 5,421,780 | A | 6/1995 | Vukovic |
| 5,499,969 | A | 3/1996 | Beuchat et al. |
| 5,501,580 | A | 3/1996 | Barrus et al. |
| 5,643,302 | A | 7/1997 | Beiser et al. |
| 5,752,813 | A | 5/1998 | Tyner et al. |
| 5,755,691 | A | 5/1998 | Hilborne |
| 5,769,618 | A | 6/1998 | Ono et al. |
| 6,000,512 | A | 12/1999 | Cronin et al. |
| 6,006,881 | A | 12/1999 | Lederman et al. |
| 6,158,996 | A | 12/2000 | Becher |
| 6,170,625 | B1 | 1/2001 | Tanaka |
| 7,070,578 | B2 | 7/2006 | Leukanech et al. |
| 7,588,385 | B2 | 9/2009 | Sugata |
| 7,779,987 | B2 | 8/2010 | Swinderman |
| 7,827,570 | B2 | 11/2010 | Suzuki |
| 8,986,252 | B2 | 3/2015 | Cummings et al. |
| 9,006,148 | B2 | 4/2015 | Zar |
| 9,033,940 | B2 | 5/2015 | Muri, I et al. |
| 9,445,943 | B2 | 9/2016 | Wilson et al. |
| 9,447,665 | B2 | 9/2016 | Morrow |
| 9,603,990 | B2 | 3/2017 | Woolford |
| 9,962,226 | B2 | 5/2018 | Brennan et al. |
| 10,280,683 | B1 | 5/2019 | Smid |
| 10,288,065 | B1 | 5/2019 | Smid et al. |
| 10,688,272 | B2 | 6/2020 | Burgess et al. |
| 10,704,351 | B2 | 7/2020 | Haugland |
| 11,371,502 | B2 | 6/2022 | Muckley et al. |
| 11,622,914 | B2 | 4/2023 | Hayman et al. |
| 2001/0011623 | A1 | 8/2001 | Ogata et al. |
| 2001/0055528 | A1 | 12/2001 | Mills |
| 2003/0000796 | A1 | 1/2003 | Kawai et al. |
| 2004/0202561 | A1 | 10/2004 | Hershberger et al. |
| 2005/0049621 | A1 | 3/2005 | Feingold et al. |
| 2005/0118048 | A1 | 6/2005 | Traxinger |
| 2006/0083637 | A1 | 4/2006 | Marielle |
| 2007/0261214 | A1 | 11/2007 | Nerbonne et al. |
| 2008/0078647 | A1 | 4/2008 | Watanabe et al. |
| 2010/0297193 | A1 | 11/2010 | Archambeau et al. |
| 2011/0137231 | A1 | 6/2011 | Sorensen et al. |
| 2012/0039734 | A1 | 2/2012 | Sakakihara |
| 2012/0063941 | A1 | 3/2012 | Overmeier et al. |

| | | | |
|---|---|---|---|
| 2012/0164006 | A1 | 6/2012 | Moy et al. |
| 2012/0271233 | A1 | 10/2012 | Brjuggemann et al. |
| 2013/0048384 | A1 | 2/2013 | Jarvis et al. |
| 2013/0071272 | A1 | 3/2013 | Juretich et al. |
| 2013/0092493 | A1 | 4/2013 | Hsueh |
| 2013/0267894 | A1 | 10/2013 | Woolford et al. |
| 2014/0163455 | A1 | 6/2014 | Wilson et al. |
| 2014/0227121 | A1 | 8/2014 | Parrett et al. |
| 2014/0311730 | A1 | 10/2014 | Morrow |
| 2016/0074565 | A1 | 3/2016 | Giordano et al. |
| 2017/0128859 | A1 | 5/2017 | Levitt et al. |
| 2017/0246602 | A1 | 8/2017 | Dean et al. |
| 2018/0010612 | A1 | 1/2018 | Wegener et al. |
| 2018/0177945 | A1 | 6/2018 | Sims et al. |
| 2019/0128342 | A1 | 5/2019 | Sturgin et al. |
| 2019/0159830 | A1* | 5/2019 | Horner .............. A61B 18/1402 |
| 2019/0210489 | A1 | 7/2019 | Sato |
| 2019/0247050 | A1 | 8/2019 | Goldsmith |
| 2019/0365567 | A1* | 12/2019 | Balkenbush ........ A61F 9/00745 |
| 2020/0121848 | A1 | 4/2020 | Schmidlin et al. |
| 2020/0200313 | A1* | 6/2020 | Chu ..................... A61M 1/772 |
| 2021/0095674 | A1 | 4/2021 | Lu et al. |
| 2021/0128808 | A1 | 5/2021 | Dandler et al. |
| 2021/0172438 | A1 | 6/2021 | Agostini et al. |
| 2022/0186792 | A1 | 6/2022 | Robert et al. |
| 2022/0241487 | A1 | 8/2022 | Sussman |
| 2022/0308517 | A1 | 9/2022 | Takagi |
| 2022/0362056 | A1 | 11/2022 | Algawi et al. |
| 2022/0362452 | A1 | 11/2022 | Algawi et al. |
| 2022/0362453 | A1 | 11/2022 | Algawi et al. |
| 2024/0139028 | A1 | 5/2024 | Shechtman et al. |
| 2024/0293609 | A1 | 9/2024 | Loomis et al. |

FOREIGN PATENT DOCUMENTS

| | | | | |
|---|---|---|---|---|
| DE | 312191 | C | 12/1917 | |
| DE | 3205222 | A1 | 8/1983 | |
| DE | 3816581 | C1 | 9/1989 | |
| DE | 4031360 | A1 | 1/1992 | |
| DE | 9312700 | U1 | 11/1993 | |
| DE | 19530978 | A1 | 2/1997 | |
| DE | 10116641 | A1 | 10/2002 | |
| DE | 102007031722 | A1 | 1/2009 | |
| DE | 102008042429 | A1 | 4/2010 | |
| DE | 102016124241 | A1 | 6/2018 | |
| DE | 102018102640 | A1 | 8/2019 | |
| JP | H09177807 | A | 7/1997 | |
| JP | 2764292 | B2 | 6/1998 | |
| JP | H10252767 | A | 9/1998 | |
| JP | 2002031153 | A | 1/2002 | |
| JP | 2007139084 | A | 6/2007 | |
| JP | 2017207565 | A | 11/2017 | |
| WO | 8903230 | A1 | 4/1989 | |
| WO | WO-2014113384 | A2 * | 7/2014 | ........... A61F 9/0017 |
| WO | 2016013504 | A1 | 1/2016 | |
| WO | 2020160434 | A1 | 8/2020 | |
| WO | 2021001742 | A1 | 1/2021 | |
| WO | 2021044440 | A1 | 3/2021 | |
| WO | 2022263951 | A1 | 12/2022 | |

* cited by examiner

IRRIGATION IN A PHACOEMULSIFICATION SYSTEM

RELATED APPLICATION INFORMATION

The present application claims benefit of U.S. Provisional Patent Application Ser. 63/210,585 of Govari, et al., filed Jun. 15, 2021, the disclosure of which is hereby incorporated herein by reference.

FIELD OF THE INVENTION

The present invention relates to medical systems, and in particular, but not exclusively to, phacoemulsification.

BACKGROUND

A cataract is a clouding and hardening of the eye's natural lens, a structure which is positioned behind the cornea, iris and pupil. The lens is mostly made up of water and protein and as people age these proteins change and may begin to clump together obscuring portions of the lens. To correct this a physician may recommend phacoemulsification cataract surgery. Before the procedure, the surgeon numbs the area with anesthesia. Then a small incision is made in the sclera or clear cornea of the eye. Fluids are injected into this incision to support the surrounding structures. The anterior surface of the lens capsule is then removed to gain access to the cataract. The surgeon then uses a phacoemulsification probe, which has an ultrasonic handpiece with a titanium or steel needle. The tip of the needle vibrates at ultrasonic frequency to sculpt and emulsify the cataract while a pump aspirates lens particles and fluid from the eye through the tip. The pump is typically controlled with a microprocessor.

The pump may be a peristaltic and/or a venturi type of pump for example. Aspirated fluids are replaced with irrigation of a balanced salt solution to maintain the anterior chamber of the eye. After removing the cataract with phacoemulsification, the softer outer lens cortex is removed with suction. An intraocular lens (IOL) is introduced into the empty lens capsule. Small struts called haptics hold the IOL in place. Once correctly implanted the IOL restores the patient's vision.

BRIEF DESCRIPTION OF THE DRAWINGS

The present invention will be understood from the following detailed description, taken in conjunction with the drawings in which.

DESCRIPTION OF EXAMPLES

Overview

Figure 1:
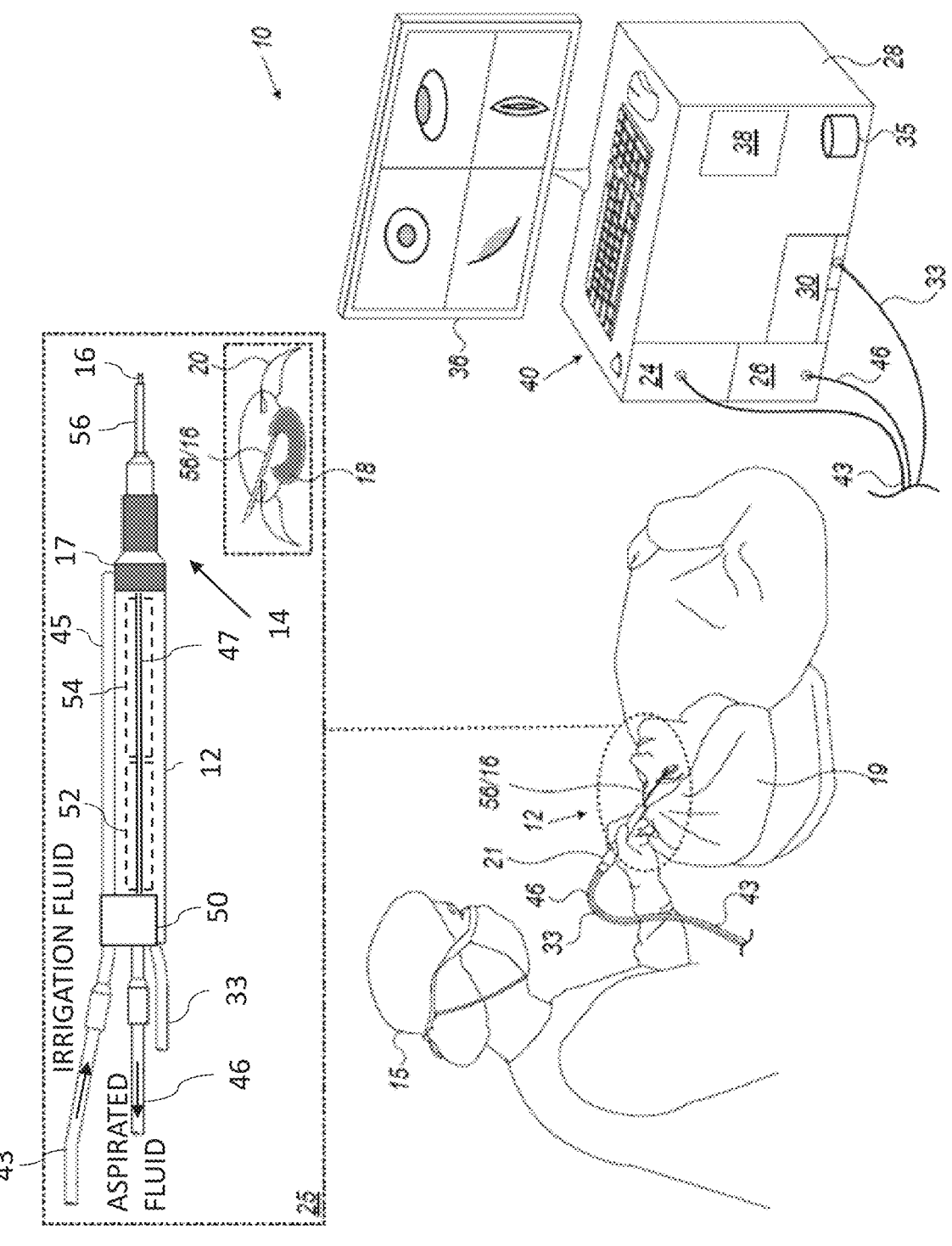
FIG. 1 is a partly pictorial, partly block diagram view of a phacoemulsification system constructed and operative in accordance with an example of the present invention.

When operating on the eye, such as performing cataract surgery, the flows of fluid into and out of the eye are critical. While performing emulsification of the cataract, aspiration is needed to both bring the cataract into contact with the needle of the phacoemulsification probe so that the needle may sculpt and emulsify the cataract and also to remove particles of the cataract from the eye. As fluid and waste matter is removed from the eye an equal amount of fluid needs to be injected into the eye to ensure that adequate fluid is in the eye at all times. Additionally, it is essential that the pressure in the eye does not exceed safe limits. Also, it is generally desired by the physician performing the cataract surgery that the fluid pressure in the eye is as stable as possible.

Therefore, during cataract surgery it is important to control the irrigation and aspiration very carefully. For example, it is important to irrigate the eye with non-oscillating or minimally oscillating flows.

Peristaltic or progressive cavity pumps may be used for different medical applications. However, peristaltic pumps have a relatively long ramp up time until they achieve a steady state making the flow rate difficult to control. Even when the pump achieves steady state, the fluid flow is oscillating. A progressive cavity pump may also be problematic. The rotor of the pump contacts the stator of the pump, leading to friction causing fragments from the stator and/or the rotor to enter the irrigation fluid. In addition, the output from the pump is pulsatory, so that the irrigation fluid is not transferred at a completely constant rate.

Therefore, embodiments of the present invention solve the above problems by adding a pressure damping insert in an irrigation line, which connects an irrigation reservoir with a needle of a phacoemulsification probe via a pumping sub-system, after the output of the pumping sub-system to dampen (e.g., reduce or smooth out) pressure elevations in the irrigation fluid exiting the pumping sub-system. In some embodiments, a filter is also added to the irrigation line after the output of the pumping sub-system to prevent fragments deposited in the irrigation fluid by the pumping sub-system from reaching the distal end of the probe. In other examples, the pressure damping insert, and the filter are formed as a unitary element to perform both pressure damping and fragment filtering. The pumping sub-system may include any suitable pump, for example, a progressive cavity pump, or a peristaltic pump.

The pressure damping insert may include multiple paths (e.g., pores or holes) therethrough dividing a flow of the irrigation fluid entering the pressure damping insert thereby damping pressure elevations in the irrigation fluid exiting the pumping sub-system.

In some examples, the pressure damping insert includes an elastic material such as expanded polytetrafluoroethylene (ePTFE) which include pores or holes therein as part of the material formation. In some examples, the pressure damping insert may be formed from a membrane such as an ePTFE membrane. In addition to the pores or holes in the elastic material dividing the flow of the irrigation fluid entering the pressure damping insert in order to dampen the pressure elevations in the irrigation fluid exiting the pumping sub-system, the elastic material deforms as a function of the pressure of the irrigation fluid on the pressure damping insert thereby enhancing damping of the pressure elevations in the irrigation fluid.

In some examples, the pressure damping insert may be formed from a mesh material, which may also be configured to filter the fragments deposited in the irrigation fluid by the pumping sub-system. An example of a suitable mesh material is a fiberglass mesh.

SYSTEM DESCRIPTION

Reference is now made to FIG. 1 is a partly pictorial, partly block diagram view of a phacoemulsification system 10 constructed and operative in accordance with an example of the present invention.

The phacoemulsification system 10 comprises a phacoemulsification probe 12 (e.g., handpiece). In some examples, the phacoemulsification probe 12 may be replaced by any suitable medical tool. As seen in the pictorial view of phacoemulsification system 10, and in inset 25, phacoemulsification probe 12 comprises a probe body 17, and a distal end 14 including a needle 16 and a coaxial irrigation sleeve 56 that at least partially surrounds needle 16 and creates a fluid pathway between the external wall of the needle and the internal wall of the irrigation sleeve. The needle 16 is generally hollow to provide an aspiration channel. Moreover, irrigation sleeve 56 may have one or more side ports at, or near, the distal end to allow irrigation fluid to flow towards the distal end 14 of the phacoemulsification probe 12 through the fluid pathway and out of the port(s).

Needle 16 is configured for insertion into a lens capsule 18 of an eye 20 of a patient 19 by a physician 15 to remove a cataract. While the needle 16 (and irrigation sleeve 56) are shown in inset 25 as a straight object, any suitable needle may be used with phacoemulsification probe 12, for example, a curved or bent tip needle commercially available from Johnson & Johnson Surgical Vision, Inc., Irvine, CA, USA.

In the example of FIG. 1, during the phacoemulsification procedure, a pumping sub-system 24 comprised in a console 28 pumps irrigation fluid from an irrigation reservoir 60 (FIG. 2) to the irrigation sleeve 56 to irrigate the eye 20. The irrigation fluid is pumped via an irrigation tubing line 43 running from the console 28 to an irrigation channel 45 of probe 12. The distal end of the irrigation channel 45 includes the fluid pathway in the irrigation sleeve 56.

Eye fluid and waste matter (e.g., emulsified parts of the cataract) are aspirated via an aspiration channel 47, which extends from the hollow of needle 16 through the phacoemulsification probe 12, and then via an aspiration tubing line 46 to a collection receptacle in the console 28. The aspiration is affected by a pumping sub-system 26, also comprised in console 28.

System 10 may include a fluid dynamics cartridge 50, which may include one or more valves to regulate the flow of fluid in the irrigation channel 45 and/or aspiration channel 47 as well as sensors. Part of the irrigation channel 45 and the aspiration channel 47 is disposed in the probe body 17 and part is disposed in the removable cartridge 50.

Phacoemulsification probe 12 includes other elements, such as a piezoelectric crystal 52 coupled to a horn 54 to drive vibration of needle 16. The piezoelectric crystal is configured to vibrate needle 16 (e.g., in a resonant vibration mode) to emulsify the lens capsule 18 of the eye 20. The vibration of needle 16 is used to break a cataract into small pieces during a phacoemulsification procedure. Console 28 comprises a piezoelectric drive module 30, coupled with the piezoelectric crystal 52, using electrical wiring running in a cable 33. Drive module 30 is controlled by a controller 38 and may convey processor-controlled driving signals via cable 33 to, for example, maintain needle 16 at maximal vibration amplitude. The drive module may be realized in hardware or software, for example, in a proportional-integral-derivative (PID) control architecture. The controller 38 may also be configured to receive signals from sensors in the phacoemulsification probe 12 and control one or more valves to regulate the flow of fluid in the irrigation channel 45 and/or the aspiration channel 47.

Controller 38 may receive user-based commands via a user interface 40, which may include setting a vibration mode and/or frequency of the piezoelectric crystal 52, and setting or adjusting an irrigation and/or aspiration rate of the pumping sub-systems 24/26. In some examples, user interface 40 and a display 36 may be combined as a single touch screen graphical user interface. In some examples, the physician 15 uses a foot pedal (not shown) as a means of control. Additionally, or alternatively, controller 38 may receive the user-based commands from controls located in a handle 21 of probe 12.

Some or all of the functions of controller 38 may be combined in a single physical component or, alternatively, implemented using multiple physical components. These physical components may comprise hard-wired or programmable devices, or a combination of the two. In some examples, at least some of the functions of controller 38 may be carried out by suitable software stored in a memory 35 (as shown in FIG. 1). This software may be downloaded to a device in electronic form, over a network, for example. Alternatively, or additionally, the software may be stored in tangible, non-transitory computer-readable storage media, such as optical, magnetic, or electronic memory.

The system shown in FIG. 1 may include further elements which are omitted for clarity of presentation. For example, physician 15 typically performs the procedure using a stereomicroscope or magnifying glasses, neither of which are shown. Physician 15 may use other surgical tools in addition to probe 12, which are also not shown in order to maintain clarity and simplicity of presentation.

Figure 2:
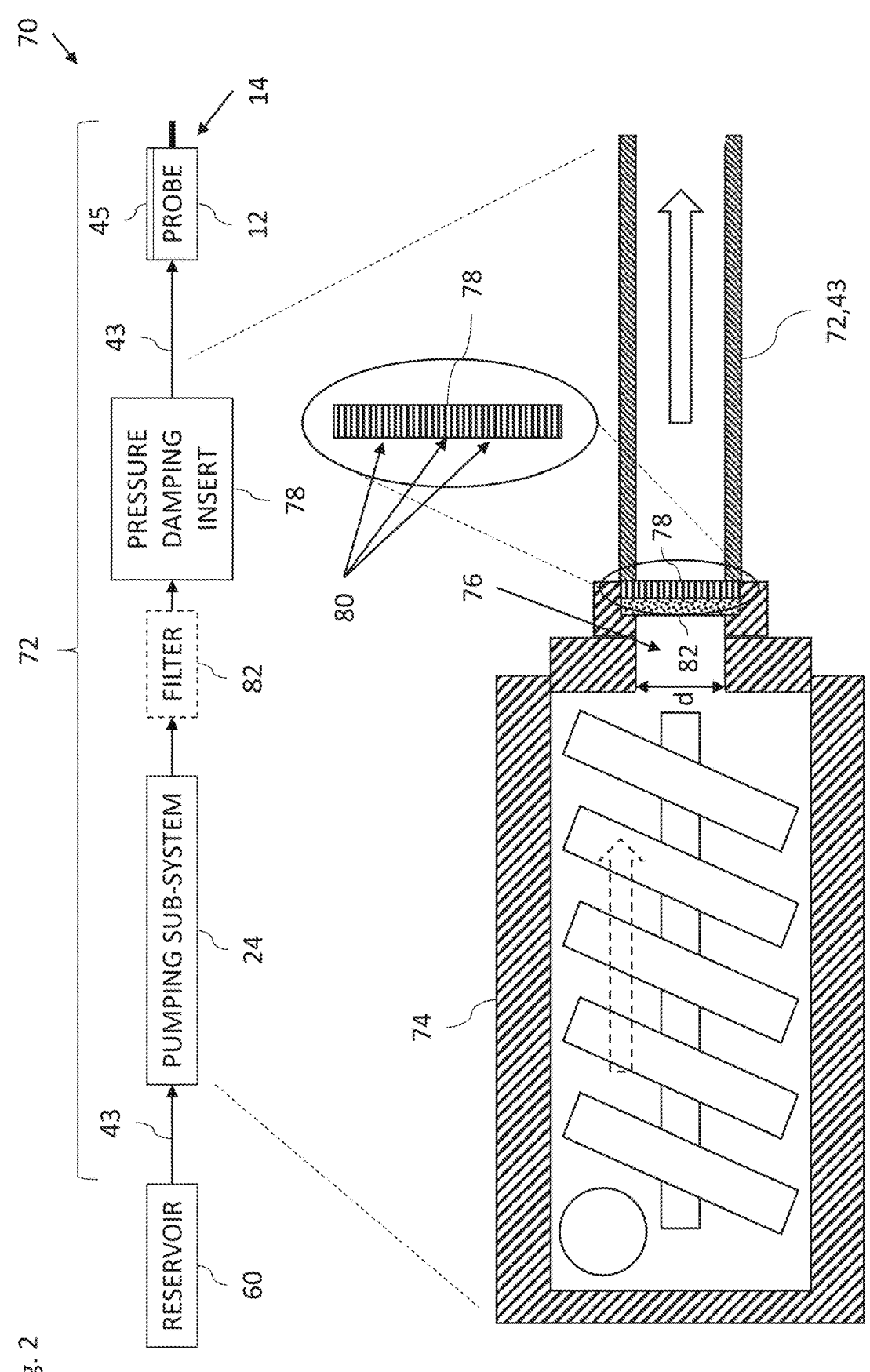
FIG. 2 is a partly pictorial, partly block diagram view of the irrigation sub-system of the phacoemulsification system of FIG. 1.

Reference is now made to FIG. 2, which is a partly pictorial, partly block diagram view of an irrigation sub-system 70 of the phacoemulsification system 10 of FIG. 1.

The irrigation sub-system 70 includes the irrigation reservoir 60 configured to store irrigation fluid (not shown). The irrigation sub-system 70 includes an irrigation line 72 (for example, including the irrigation tubing line 43 and the irrigation channel 45) extending from the irrigation reservoir 60 to the distal end 14 of phacoemulsification probe 12.

The irrigation sub-system 70 includes the pumping sub-system 24, which is configured to pump the irrigation fluid from the irrigation reservoir 60 to the distal end 14 of the phacoemulsification probe 12 via the irrigation line 72. The pumping sub-system 24 may include any suitable pump 74, for example, a progressive cavity pump, or a peristaltic pump. The diameter d of an outlet 76 of the pump 74 may have any suitable value, for example, in a range between 3-10 mm.

The irrigation sub-system 70 also includes a pressure damping insert 78 disposed in the irrigation line 72 (e.g., across the line) between the pumping sub-system 24 and the distal end 14. The pressure damping insert 78 is typically disposed between the outlet 76 of the pump 74 and the irrigation tubing line 43 as shown in FIG. 2. The pressure damping insert 78 includes multiple paths 80 therethrough (only some labeled for the sake of simplicity) configured to divide a flow of the irrigation fluid entering the pressure damping insert 78 in order to dampen pressure elevations in the irrigation fluid exiting the pumping sub-system 24. The paths 80 may be formed in the pressure damping insert 78 by drilling holes (e.g., using laser drilling) or by selecting a material (e.g., ePTFE) for the pressure damping insert 78 that includes holes or pores to form the paths 80, as described in more detail below. The pressure damping insert 78 may include any suitable number of paths 80, and may depend on one or more of the following: the size of the outlet 76, the power and/or speed of the pump 74, the size of the pressure elevations caused by the pump 74, and/or the width and/or diameter of each of the paths 80. Similarly, the width and/or diameter of each of the paths may be any suitable size, and may depend on one or more of the following: the size of the outlet 76, the power and/or speed of the pump 74, the size of the pressure elevations caused by the pump 74, and/or the number of paths 80.

The irrigation sub-system 70 may optionally include a filter 82 disposed in the irrigation line 72 between the pumping sub-system 24 and the distal end 14 of the phacoemulsification probe 12 configured to prevent fragments deposited in the irrigation fluid by the pumping sub-system 24 from reaching the distal end 14. In some examples, the filter 82 is disposed in the irrigation line 72 between the pump 74 and the pressure damping insert 78. In some examples, the filter 82 is configured to filter fragments smaller than 20 microns (e.g., 0.5 microns or 1 micron). In some examples, the filter 82 and the pressure damping insert 78 are comprised in a unitary item. For example, the pressure damping insert 78 may be configured to filter fragments (e.g., smaller than 20 microns) deposited in the irrigation fluid by the pumping sub-system 24.

The pressure damping insert 78 may include or be formed from any suitable material. In some examples, the pressure damping insert 78 includes an elastic material. The elastic material may include, as part of the formation of the elastic material, pores or holes forming the multiple paths 80. In addition to the pores or holes in the elastic material dividing the flow of the irrigation fluid entering the pressure damping insert 78 in order to dampen the pressure elevations in the irrigation fluid exiting the pumping sub-system 24, the elastic material deforms as a function of the pressure of the irrigation fluid on the pressure damping insert 78 thereby enhancing damping of the pressure elevations in the irrigation fluid.

An example of the elastic material is expanded polytetrafluoroethylene (ePTFE). The pores or holes of the elastic material may filter fragments deposited in the irrigation fluid. The pores or holes may have any suitable size (e.g., diameter), for example, in a range between 0.5 and 20 microns. In some examples, the pressure damping insert 78 may include (or be formed from) an ePTFE membrane having a thickness between 50 and 300 microns, for example. The pores of the ePTFE membrane may have any suitable size (e.g., diameter), for example, in a range between 0.5 and 20 microns.

In some examples, the pressure damping insert 78 may include (or be formed from) a mesh material. In some examples, the mesh material may also be configured to filter fragments (e.g., smaller than 20 microns) deposited in the irrigation fluid by the pumping sub-system. An example of a suitable mesh material is a fiberglass mesh.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 72% to 108%.

EXAMPLES

Example 1: A phacoemulsification system, comprising: a phacoemulsification probe including: a distal end comprising a needle; and a piezoelectric crystal configured to vibrate the needle so as to emulsify a lens of an eye; an irrigation reservoir configured to store irrigation fluid; an irrigation line extending from the irrigation reservoir to the distal end of phacoemulsification probe; a pumping sub-system configured to pump the irrigation fluid from the irrigation reservoir to the distal end of the phacoemulsification probe via the irrigation line; and a pressure damping insert disposed in the irrigation line between the pumping sub-system and the distal end, and comprising multiple paths therethrough configured to divide a flow of the irrigation fluid entering the pressure damping insert in order to dampen pressure elevations in the irrigation fluid exiting the pumping sub-system.

Example 2: The system according to example 1, further comprising a filter disposed in the irrigation line between the pumping sub-system and the distal end configured to prevent fragments deposited in the irrigation fluid by the pumping sub-system from reaching the distal end.

Example 3: The system according to example 2, wherein the filter is configured to filter fragments smaller than 20 microns.

Example 4: The system according to example 2 or 3, wherein the filter and the pressure damping insert are comprised in a unitary item.

Example 5: The system according to any of examples 1-4, wherein the pressure damping insert includes an elastic material forming the multiple paths.

Example 6: The system according to example 5, wherein the elastic material includes pores forming the multiple paths.

Example 7: The system according to example 6, wherein the elastic material includes expanded polytetrafluoroethylene (ePTFE).

Example 8: The system according to example 7, wherein the size of each of the pores in between 0.5 and 20 microns.

Example 9: The system according to example 7, wherein the insert includes an ePTFE membrane having a thickness between 50 and 300 microns.

Example 10: The system according to any of examples 1-9, wherein the pressure damping insert includes a mesh material.

Example 11: The system according to example 10, wherein the mesh material includes fiberglass.

Various features of the invention which are, for clarity, described in the contexts of separate examples may also be provided in combination in a single example. Conversely, various features of the invention which are, for brevity, described in the context of a single example may also be provided separately or in any suitable sub-combination.

The examples described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:

1. A phacoemulsification system, comprising:
   a phacoemulsification probe including:
      a distal end comprising a needle; and
      a piezoelectric crystal configured to vibrate the needle so as to emulsify a lens of an eye;
   an irrigation reservoir configured to store irrigation fluid;
   an irrigation line extending from the irrigation reservoir to the distal end of phacoemulsification probe;
   a pumping sub-system configured to pump the irrigation fluid from the irrigation reservoir to the distal end of the phacoemulsification probe via the irrigation line; and a pressure damping insert disposed in the irrigation line between the pumping sub-system and the distal end, and comprising multiple paths therethrough configured to divide a flow of the irrigation fluid entering the pressure damping insert in order to dampen pressure elevations in the irrigation fluid exiting the pumping sub-system.

2. The system according to claim 1, further comprising a filter disposed in the irrigation line between the pumping sub-system and the distal end configured to prevent fragments deposited in the irrigation fluid by the pumping sub-system from reaching the distal end.

3. The system according to claim 2, wherein the filter is configured to filter fragments smaller than 20 microns.

4. The system according to claim 2, wherein the filter and the pressure damping insert are comprised in a unitary item.

5. The system according to claim 1, wherein the pressure damping insert includes an elastic material forming the multiple paths.

6. The system according to claim 5, wherein the elastic material includes pores forming the multiple paths.

7. The system according to claim 6, wherein the elastic material includes expanded polytetrafluoroethylene (ePTFE).

8. The system according to claim 7, wherein a size of each of the pores in between 0.5 and 20 microns.

9. The system according to claim 7, wherein the pressure damping insert includes an ePTFE membrane having a thickness between 50 and 300 microns.

10. The system according to claim 1, wherein the pressure damping insert includes a mesh material.

11. The system according to claim 10, wherein the mesh material includes fiberglass.

* * * * *